(12) United States Patent
Limketkai et al.

(10) Patent No.: US 10,583,147 B2
(45) Date of Patent: Mar. 10, 2020

(54) COMPOSITIONS CONTAINING CYCLODEXTRIN-BASED METAL ORGANIC FRAMEWORKS

(71) Applicant: PanaceaNano, Inc., Laguna Niguel, CA (US)

(72) Inventors: Benjie N. Limketkai, Hesperia, CA (US); Youssry Y. Botros, Laguna Niguel, CA (US)

(73) Assignee: PanaceaNano, Inc., Aliso Viejo, CA (US)

(*) Notice: Subject to any disclaimer, the term of this patent is extended or adjusted under 35 U.S.C. 154(b) by 0 days.

(21) Appl. No.: 15/467,016

(22) Filed: Mar. 23, 2017

(65) Prior Publication Data

US 2017/0274097 A1 Sep. 28, 2017

Related U.S. Application Data

(60) Provisional application No. 62/312,964, filed on Mar. 24, 2016.

(51) Int. Cl.
| | | |
|---|---|---|
| *A61K 31/60* | (2006.01) | |
| *A61K 47/46* | (2006.01) | |
| *A61K 47/69* | (2017.01) | |
| *A61K 9/00* | (2006.01) | |
| *A61K 47/40* | (2006.01) | |

(52) U.S. Cl.
CPC ........... *A61K 31/60* (2013.01); *A61K 9/0014* (2013.01); *A61K 47/40* (2013.01); *A61K 47/46* (2013.01); *A61K 47/6951* (2017.08)

(58) Field of Classification Search
CPC ...... A61K 9/0014; A61K 31/60; A61K 47/40; A61K 47/46; A61K 47/6951
See application file for complete search history.

(56) References Cited

U.S. PATENT DOCUMENTS

| | | | |
|---|---|---|---|
| 2,886,446 A | 5/1959 | Kramer et al. | |
| 3,258,400 A | 6/1966 | Houlihan | |
| 3,920,849 A | 11/1975 | Marmo et al. | |
| 3,939,099 A | 2/1976 | Tusa et al. | |
| 4,252,986 A | 2/1981 | Klein et al. | |
| 4,303,787 A | 12/1981 | Horikoshi et al. | |
| 4,384,898 A | 5/1983 | Okada et al. | |
| 4,568,560 A | 2/1986 | Schobel | |
| 4,808,232 A | 2/1989 | Beesley | |
| 4,835,105 A | 5/1989 | Seres et al. | |
| 4,849,400 A | 7/1989 | King | |
| 5,051,305 A | 9/1991 | Whitaker, Sr. | |
| 5,238,915 A | 8/1993 | Fuwa et al. | |
| 6,110,449 A | 8/2000 | Bacon et al. | |
| 6,172,037 B1 | 1/2001 | Perring et al. | |
| 6,177,413 B1 | 1/2001 | Blahut | |
| 6,458,754 B1 | 10/2002 | Velazquez et al. | |
| 6,558,706 B2 | 5/2003 | Kantor et al. | |
| 6,660,804 B1 | 12/2003 | Weltrowski et al. | |
| 8,709,072 B2 | 4/2014 | Rahi et al. | |
| 8,871,473 B2 | 10/2014 | Wu | |
| 9,085,460 B2 | 7/2015 | Stoddart et al. | |
| 9,399,803 B2 | 7/2016 | Stoddart et al. | |
| 2003/0092600 A1 | 5/2003 | Shepherd, Jr. | |
| 2005/0255069 A1 | 11/2005 | Muller | |
| 2008/0054089 A1 | 3/2008 | Oldfield et al. | |
| 2008/0206823 A1 | 8/2008 | Jacobson et al. | |
| 2011/0052650 A1 | 3/2011 | Morris et al. | |
| 2012/0070904 A1 | 3/2012 | Stoddart et al. | |
| 2013/0171228 A1* | 7/2013 | Morris ................... | A01N 25/10 424/409 |
| 2013/0313193 A1 | 11/2013 | Nair et al. | |
| 2014/0105842 A1 | 4/2014 | Pan et al. | |
| 2014/0220112 A1 | 8/2014 | Szoka, Jr. et al. | |
| 2014/0311298 A1 | 10/2014 | Stoddart et al. | |
| 2015/0150981 A1 | 6/2015 | Gref et al. | |
| 2015/0322174 A1 | 11/2015 | Stoddart et al. | |
| 2017/0136128 A1* | 5/2017 | Hartlieb ............... | A61K 31/192 |
| 2017/0189890 A1 | 7/2017 | Holcroft et al. | |
| 2017/0203073 A1* | 7/2017 | Dor-Zidon ........ | A61M 16/1075 |
| 2018/0147284 A1* | 5/2018 | Orellana-Tavra ...... | A61K 47/12 |

FOREIGN PATENT DOCUMENTS

| | | |
|---|---|---|
| CN | 104888235 A | 9/2015 |
| CN | 105153328 A | 12/2015 |
| JP | H05-076756 A | 3/1993 |
| WO | 2007035596 A2 | 3/2007 |

(Continued)

OTHER PUBLICATIONS

Hongjun Lu, Xiaoning Yang, Shuxian Li, Yu Zhang, Jingquan Sha, Changde Li, Jingwen Sun, "Study on a new cyclodextrin based metal-organic framework with chiral helices", Inorganic Chemistry Communications 61 (2015) 48-52. (Year: 2015).*

Wataru Michida, Masato Ezaki, Mina Sakuragi, Guoqing Guan, Katsuki Kusakabe, "Crystal growth of cyclodextrin-based metal-organic framework with inclusion of ferulic acid", Crystal Research and Technology, 2015, 50(7), 556. (Year: 2015).*

Thorsteinn Loftsson and Mar Masson, "Cyclodextrins in topical drug formulations: theory and practice", International Journal of Pharmaceutics, 225 (2001), 15-30. (Year: 2001).*

Hajime Matsuda and Hidetoshi Arima, "Cyclodextrins in transdermal and rectal delivery", Advanced Drug Delivery Reviews, 36 (1999), 81-99. (Year: 1999).*

(Continued)

*Primary Examiner* — Mina Haghighatian
*Assistant Examiner* — Nathan W Schlientz (57) ABSTRACT

This disclosure relates to a composition that includes an active agent and a porous cyclodextrin-based metal organic framework (CD-MOF). The CD-MOF includes at least a metal cation and a plurality of cyclodextrin molecules. The composition includes from about 0.05 mg to about 0.5 mg of the active agent per 1 mg of the CD-MOF. Methods of preparing and using the compositions are also disclosed.

16 Claims, 7 Drawing Sheets

(56) References Cited

FOREIGN PATENT DOCUMENTS

| WO | 2014095427 A1 | 6/2014 |
| WO | 2016010522 A1 | 1/2016 |

OTHER PUBLICATIONS

Wind, et al.; "Engineering of factors determining a-amylase and cyclodextrin glycosyltransferase specificity in the cyclodextrin glycosyltransferase from Thermoanaerobacterium thermosulfurigenes EM1"; Jan. 6/Feb. 23, 1998; pp. 598-605.

McKinlay, et al.; "BioMOFs: Metal-Organic Frameworks for Biological and Medical Applications"; 2010; pp. 6260-6266.

Smaldone, et al.; "Metal-Organic Frameworks from Edible Natural Products"; 2010; pp. 8630-8634.

Gassensmith, et al.; "Strong and Reversible Binding of Carbon Dioxide in a Green Metal-Organic Framework"; 2011; pp. 15312-15315.

Forgan, et al.; "Nanoporous Carbohydrate Metal-Organic Frameworks"; 2012; pp. 406-417.

Gassensmith, et al.; "A Metal-Organic Framework-Based Material for Electrochemical Sensing of Carbon Dioxide"; 2014; pp. 8277-8282.

Gassensmith, et al.; "A Metal-Organic Framework-Based Material for Electrochemical Sensing of Carbon Dioxide"; Supplementary Information; 2014; pp. S1-S12.

Liu, et al.; "Second-Sphere Coordination Revisited"; 2014; pp. 315-320.

Liu, et al.; "Extended metal-carbohydrated frameworks"; 2014; pp. 1-14.

An, et al.; "Cation-Triggered Drug Release from f Porous Zinc-Adeninate Metal-Organic Framework"; JACS Communications; University of Pittsburgh; 2009 American Chemical Society, vol. 131, No. 24; Apr. 14, 2009; pp. 8376-8377.

Zhou, et al.; "β-Cyclodextrin inclusion complex: preparation, characterization, and its aspirin release in vitro"; Front. Mater. Sci. 2012, 6(3); Research Article; The Chemical Engineering & Phamaceutics College, Henan University of Science and Technology, Luoyang, China; Jun. 19, 2012; pp. 259-267.

Bemini, et al.; "Screening of bio-compatible metal-organic framesworks as potential drug carriers using Monte Carlo simulations"; Journal of Materials Chemistry B; Royal Society of Chemistry; www.rsc.org/MaterialsB; DOI: 10.1039/c3tb21328e; Nov. 22, 2013; 9 pgs.

Sha, et al.; "Synthesis and structure of new carbohydrate metal-organic frameworks and inclusion complexes"; Elsevier; Journal of Molecular Structure; www/elsevier.com; Aug. 13, 2015; 6 pgs.

Sha, et al.; "Unprecedented α-cyclodextrin metal-organic frameworks with chirality: Structure and drug adsorptions"; Elsevier; Polyhedron; www.elsevier.com/locate/poly; Oct. 19, 2016; 7 pgs.

Sha, et al.; "Nontoxic and renewable metal-organic framework based on α-cyclodextrin with efficient drug delivery"; RSC Advances; Royal Society of Chemistry; www.rsc.org/advances; DOI: 10.1039/c6ra16549d; Aug. 16, 2016; 7 pgs.

Liu, et al.; "Optimized synthesis and crystalline stability of γ-cyclodextrin metal-organic frameworks for drug adsorption"; Elsevier; International Journal of Pharmaceutics; www.elsevier.com/locate/ijpharm; Apr. 21, 2016; 8 pgs.

Liu, et al.; "Supporting Information for Optimized synthesis and crystalline stability of γ-cyclodextrin metal-organic frameworks for drug adsorption"; International Journal of Pharmaceutics; Sep. 29, 2016; 8 pgs.

* cited by examiner

COMPOSITIONS CONTAINING CYCLODEXTRIN-BASED METAL ORGANIC FRAMEWORKS

CROSS-REFERENCE TO RELATED APPLICATION

This application claims the benefit of U.S. Provisional Application Ser. No. 62/312,964, filed by Benjie N. Limketkai, et al. on Mar. 24, 2016, entitled "COMPOSITIONS CONTAINING CYCLODEXTRIN-BASED ORGANIC FRAMEWORKS," the contents of which is hereby incorporated by reference in its entirety.

TECHNICAL FIELD

This disclosure relates to compositions containing at least one active agent and at least one cyclodextrin-based metal organic framework (CD-MOF), as well as related components, products, and methods.

BACKGROUND

Cyclodextrins (cyclic dextrins, cyclic oligosaccharides, CDs) are cyclic structures composed of D-glucopyranosyl residues linked in a ring by $\alpha$-1,4 glycosidic bonds. Glucose molecules, bonded together in the ring, form a hollow, circular, truncated cone with a hydrophobic interior and a hydrophilic exterior. This structure gives CDs the ability to host guest molecules (complexant) within their cavity. Due to this ability to form inclusion compounds (complex) with a wide variety of chemicals, thereby acting as a carrier to encapsulate, stabilize, and/or alter the chemical and physical properties, e.g., volatility and solubility, of the guest molecules, CDs have been widely used in the agricultural, food, pharmaceutical, and chemical industries. The common $\alpha$CD, $\beta$CD, and $\gamma$CD consist of six, seven, and eight glucopyranose units in their ring, respectively.

SUMMARY

One embodiment of the disclosure is a composition comprising an active agent and a porous cyclodextrin-based metal organic framework (CD-MOF). The CD-MOF includes at least a metal cation and a plurality of cyclodextrin molecules. The composition includes from about 0.05 mg to about 0.5 mg of the active agent per 1 mg of the CD-MOF.

In some embodiments, the composition can include from about 0.06 mg to about 0.3 mg (e.g., from about 0.1 mg to about 0.3 mg) or from about 0.05 mg to about 0.1 mg of the active agent per 1 mg of the CD-MOF.

In some such embodiments, the active agent can have a water solubility of at least about 10 mg/mL at 25° C.

In some such embodiments, the active agent can be an acid, a vitamin, a pro-vitamin, a humectant, an antibacterial agent, or an antifungal agent. In some embodiments, the active agent can be an alpha hydroxy acid, ascorbic acid, niacinamide, panthenol, vitamin C, vitamin B, triethylene glycol, tripropylene glycol, propylene glycol, polypropylene glycol, glycerin, sorbitol, hexylene, butylene glycol, urea, a sulfonamide, tetracycline hydrochloride, triclosan, bacitracin, polymyxin B, neomycin, gentamycin, meclocycline, sulfacetamide sodium, an imidazole, a triazole, or a triazole.

In some such embodiments, the active agent can be a keratolytic agent, an antibacterial agent, an antifungal agent, an antiviral agent, an antiparasitic agent, a sunscreen agent, a vitamin, a pro-vitamin, an antipruritic agent, an analgesic agent, an anesthetic agent, or a nonsteroidal anti-inflammatory drug.

In some such embodiments, the active agent can be a beta hydroxy acid, benzoyl peroxide, allantoin, sulfur, a sulfonamide, a mupirocin, erythromycin, clindamycin, acyclovir, penciclovir, docosanol, selenium disulfide, zinc pyrithione, permethrin, lindane, crotamiton, oxybenzone, avobenzone, octisalate, octocrylene, homosalate, octinoxate, retinol, retinol palmitate, tocopherol, tocotrienol, zinc pyrithione, benzocaine, butamben, dibucaine, lidocaine, tetracaine, pramocaine, proxymetacaine, prilocaine, diclofenac, fentanyl, capsaicin, a salicylate, an antihistamine, a corticosteroid, ibuprofen, or naproxen.

In any such embodiments, the composition can further comprise a carrier that is or includes an oil solvent or an organic solvent. In any such embodiments, the composition can further comprise a carrier that is or includes an ester, an alcohol, a ketone, an ether, or a hydrocarbon solvent. In any such embodiments, the composition can further comprise a carrier that is an aqueous solvent where the composition of the active agent and the CD-MOF is at least about 10 wt % to at most about 90 wt % of the carrier. In any such embodiments, the composition can further comprise a carrier a mixture of an oil solvent and an aqueous solvent having a ratio in a range from about 10:90 to about 90:10. In any such embodiments, the composition can further comprise a carrier a mixture of an organic solvent and an aqueous solvent having a ratio in a range from about 90:10 to about 50:50.

In any such embodiments, the CD-MOF can have an average particle size of from about 10 nm to about 1 µm or from about 1 µm to about 1 cm. In some embodiments, the CD-MOF has an average particle size of from about 10 nm to about 1 µm and the composition is a suspension, emulsion or a gel in a carrier including an oil solvent, an organic solvent, an aqueous solvent or a mixture thereof. In some embodiments, the CD-MOF has an average particle size of from about 1 µm to about 1 cm and the composition is an emulsion or a gel in a carrier including an oil solvent, an organic solvent, an aqueous solvent or a mixture thereof.

Another embodiment is a method that includes treating a subject's skin with at least one of the compositions described above to form a treated area on the skin, and applying water or force to the treated area.

In any such embodiments, when the composition is applied to a subject's skin, the composition can release 50 wt % of the active agent at least about 1 hour after the application of the water to the treated area. In any such embodiments, when the composition is applied to a subject's skin, the composition can release at least about 50 wt % of the total amount of the active agent in the composition at 24 hours after application.

Other features, objects, and advantages of the invention will be apparent from the description, drawings, and claims.

DESCRIPTION OF DRAWINGS

Reference is now made to the following descriptions taken in conjunction with the accompanying drawings, in which.

Like reference symbols in the various drawings indicate like elements.

DETAILED DESCRIPTION

This disclosure generally relates to compositions containing at least one active agent and at least one CD-MOF (also referred to herein as a CD-MOF complex), as well as methods of making and using of such compositions. This disclosure benefits from the unexpected discovery that adding a CD-MOF into a composition containing an active agent (e.g., a cosmetically or therapeutically active agent) can significantly improve the release profile of the active agent (e.g., by increasing the average release rate, the effective release duration, and/or the total release amount of the active agent).

In some embodiments, the active agent can be a cosmetically active agent, a therapeutically active agent, or a topical agent.

As used herein, a cosmetically active agent refers to an agent that cures, relieves, improves, alters, affects, ameliorates, or prevents one or more cosmetic conditions or dermatological disorders. Examples of cosmetic conditions and dermatological disorders include promoting wound healing, general care of skin, hair, nail, or oral mucosa, oral diseases, gum diseases, dry skin, acne, ichthyosis, psoriasis, eczema, sunburns, insect bites, changes or damage to skin, nail or hair, and signs of skin, nail and hair changes associated with intrinsic and/or extrinsic aging (e.g., wrinkles).

As used herein, a therapeutically active agent refers to an agent that confers a therapeutic effect on a treated patient. For examples, the therapeutically active agent can cure, relieve, improve, alter, affect, ameliorate, or prevent one or more diseases, conditions, or disorders. Examples of such diseases, conditions, or disorders include infections (e.g., bacterial, viral, fungal, or parasitic infections), inflammations, allergic reactions, pain (e.g., chronic pain), skin diseases (e.g., xeroderma, ichthyosis, psoriasis, or eczema), or cancers (e.g., skin cancers). A complete list of diseases, conditions, or disorders can be found in the ICD-10 published by the World Health Organization, the contents of which are incorporated herein by reference.

As used herein, a topical agent refers to a cosmetically or therapeutically active agent that can be used in a topical composition (such as those described above), or a topically acceptable carrier, excipient, or additive. Examples of topically acceptable carriers, excipients, or additives include penetration enhancers (e.g., glycols such as propylene glycol), fixatives, emulsifiers (such as surfactants), colorants (e.g., dyes or pigments), antioxidants, preservatives, humectants, oils, thickening agents, and silicones.

Examples of the suitable active agents can include acids, vitamins, pro-vitamins, humectants, antibacterial agents, antifungal agents, antiviral agents, antiparasitic agents, keratolytic agents, sunscreen agents, antipruritic agents, analgesic agents, anesthetic agents, and nonsteroidal anti-inflammatory drugs (NSAIDs). Examples of acids that can be used as an active agent include alpha hydroxy acids (e.g., glycolic acid, lactic acid, malic acid, citric acid, or tartaric acid), and beta hydroxy acids (e.g., salicylic acid). Examples of vitamins and pro-vitamins can include vitamin C, vitamin B, ascorbic acid, niacinamide, panthenol, retinol, retinol palmitate, tocopherol, and tocotrienol. Examples of humectants can include glycerol, triethylene glycol, tripropylene glycol, propylene glycol, polypropylene glycol, glycerin, sorbitol, hexylene, butylene glycol, and urea.

Examples of keratolytic agents can include beta hydroxy acids, benzoyl peroxide, allantoin, and sulfur. Examples of sunscreen agents can include oxybenzone, avobenzone, octisalate, octocrylene, homosalate, octinoxate, zinc oxide, and titanium dioxide. Examples of antibacterial agents can include sulfonamides, tetracycline hydrochloride, triclosan, bacitracin, polymyxin B, neomycin, mupirocin, erythromycin, clindamycin, gentamycin, meclocycline, and sulfacetamide sodium. Examples of antifungal agents can include imidazoles, triazoles, triazoles, selenium disulfide, and zinc pyrithione. Examples of antiviral agents can include acyclovir, docosanol, and penciclovir. Examples of antiparasitic agents can include permethrin, lindane, and crotamiton. Examples of antipruritic agents can be antihistamines (e.g., diphenhydramine) and corticosteroids (e.g., hydrocortisone). Examples of analgesic agents can include fentanyl and capsaicin. Examples of anesthetic agents can include benzocaine, butamben, dibucaine, lidocaine, tetracaine, pramocaine, proxymetacaine, and prilocaine. Examples of NSAIDs can include diclofenac, salicylates, ibuprofen and naproxen.

In some embodiments, the active agent can be water soluble. As used herein, a water soluble active agent refers to an agent having a water solubility of at least about 10 mg/mL at 25° C. In such embodiments, the active agent can be an acid, a vitamin, a pro-vitamin, a humectant, an antibacterial agent, or an antifungal agent.

In some embodiments, the active agent can be water insoluble. As used herein, a water insoluble active agent refers to an agent having a water solubility of at most about 10 mg/mL at 25° C. In such embodiments, the active agent can be a keratolytic agent, an antibacterial agent, an antifungal agent, an antiviral agent, an antiparasitic agent, a sunscreen agent, a vitamin, a pro-vitamin, an antipruritic agent, an analgesic agent, an anesthetic agent, or a non-steroidal anti-inflammatory drug.

In some embodiments, the compositions described herein can include from at least about 0.05 mg (e.g., at least about 0.06 mg, at least about 0.1 mg, at least about 0.2 mg, at least about 0.3 mg, or at least about 0.4 mg) to at most about 0.5 mg (e.g., at most about 0.4 mg, at most about 0.3 mg, at most about 0.2 mg, at most about 0.1 mg, or at most about 0.75 mg) of the active agent per 1 mg of the CD-MOF. Without wishing to be bound by theory, it is believed that, when the compositions contain an active agent and a CD-MOF at an appropriate ratio (such as those described above), the compositions can exhibit significantly improved release profile (e.g., by increasing the average release rate, the effective release duration, and/or the total release amount of the active agent) when the compositions are applied to the skin of a subject (e.g., a patient). If the active agent to CD-MOF ratio is too high, the CD-MOF may not have a significant effect on modifying the release profile of the active agent. If the active agent to CD-MOF ratio is too low, the CD-MOF may significantly suppress the release of the active agent from the composition.

In some embodiments, the active agent can range from at least about 0.1 wt % (e.g., at least about 0.2 wt %, at least about 0.3 wt %, at least about 0.4 wt %, at least about 0.5 wt %, at least about 1 wt %, at least about 2 wt %, at least about 3 wt %, at least about 4 wt %, at least about 5 wt %) to at most about 40 wt % (e.g., at most about 30 wt %, at most about 20 wt %, at most about 10 wt %, at most about 9 wt %, at most about 8 wt %, at most about 7 wt %, at most about 6 wt %, at most about 5 wt %, at most about 3 wt %, at most about 1 wt %, at most about 0.75 wt %, or at most about 0.5 wt %) of the compositions described herein.

In general, the CD-MOFs that can be used in the compositions described herein can be those described in U.S. Pat. No. 9,085,460, the contents of which are hereby incorporated by reference in their entirely.

The CD-MOFs generally include at least one metal cation (e.g., a plurality of metal cations) and a plurality of cyclodextrin components (such as those of Formula (I) below). The at least one metal cation is generally coordinated with the plurality of cyclodextrin molecules or cyclodextrin derivatives. In general, the CD-MOFs are porous.

Suitable metal cations that can be used in the CD-MOFs include Group I metal cations (e.g., $Na^+$, $K^+$, $Rb^+$, or $CS^+$), Group II metal cations (e.g., $Mg^{2+}$, $Ca^{2+}$, $Sr^{2+}$, or $Ba^{2+}$), and transition metal cations (e.g., $Mn^{4+}$, $Fe^{3+}$, $Co^{2+}$, $Ni^{2+}$, $Cu^{2+}$, or $Zn^{2+}$). The metal cations can be included into the CD-MOFs by using salts or bases as starting materials. Examples of suitable salts include KF, KCl, KBr, $K_2CO_3$, $K_2$(azobenzene-4,4'-dicarboxylate), $Na_2CO_3$, and $NaBPh_4$. Examples of suitable bases include KOH, NaOH, RbOH, and CsOH.

In general, the main building block for CD-MOFs is cyclodextrin (CD), a cyclic oligosaccharide that includes monosaccharide residues linked in a circular ring. Suitable cyclodextrins that can be used in the CD-MOFs include, for example, α-, β- and γ-cyclodextrins. The structure of α-1,4-linked D-glucopyranosyl residue that can be used to form a building block in a cyclodextrin and the structure of a γ-cyclodextrin ring are shown in U.S. Pat. No. 9,085,460. Cyclodextrins can be mass-produced through enzymatic degradation of a renewable source (e.g., starch). In some embodiments, a CD-MOF can be made from one or more cyclodextrin derivatives (such as those shown in Formula (I) below).

Generally, CD-MOFs can be prepared by dissolution of both the cyclodextrin component (e.g., γ-cyclodextrin) and the metal-containing component (such as a metal salt (e.g., KCl) or a base containing a metal cation (e.g., KOH)) in a solvent (e.g., water) in which both have good solubility. Isolation of CD-MOFs can be achieved by addition of a poor solvent in which either of the above components has poor solubility. Suitable poor solvents include $C_1$-$C_{18}$ alcohols (e.g., methanol or ethanol), acetone, tetrahydrofuran, dioxane, acetonitrile, and a mixture thereof.

In some embodiments, CD-MOFs can be prepared by the following method. At ambient temperatures and pressures, γ-CD can be dissolved in an aqueous solution containing an alkali metal cation (e.g., $K^+$), and followed by vapor diffusion of a water-miscible solvent (e.g., methanol) to form millimeter-sized body-centered cubic crystalline structures. Without wishing to be bound by theory, it is believed that the γ-CD rings adopt the faces of a cube, with their primary (1°) faces (C6 hydroxy (OH) groups) pointing towards the interior of the cube and their secondary (2°) faces (C2 and C3 OH groups) pointing outward. Further, without wishing to be bound by theory, it is believed that the γ-CD rings are linked together by coordination of the alkali metal cations to the primary C6 OH groups and the glycosidic ring oxygen atoms. The individual cubes pack to form the body-centered cubic crystal through coordination of more alkali metal cations to the C2 and C3 OH groups of the secondary faces of the γ-CD rings. Examples of the CD-MOF geometry are illustrated in U.S. Pat. No. 9,085,460.

In some embodiments, the CD-MOFs described herein include a CD component and a metal-containing component. The metal-containing component can have the formula MN. M can be a Group I, Group II metal or transition metal, and N can be an organic or inorganic, monovalent or multivalent anion. Suitable inorganic anions include, for example, chloride, fluoride, hydroxide, sulfide, sulfinate, carbonate, chromate, and cyanide. Suitable organic anions include, for example, benzoate, azobenzene-4,4'-dicarboxylate, acetate, and oxalate. The CD component of the CD-MOFs can be a compound of the Formula (I):

(I)

in which n=0-10; each R, independently, is selected from the group consisting of —OH; —NR'R"; $C_1$-$C_{18}$ alkyl optionally substituted with one, two, three, four or five $R_1$ groups; $C_2$-$C_{18}$ alkenyl optionally substituted with one, two, three, four or five $R_1$ groups; $C_2$-$C_{18}$ alkynyl optionally substituted with one, two, three, four or five $R_1$ groups; $C_1$-$C_{18}$ alkoxy optionally substituted with one, two, three, four or five $R_1$ groups; —S(=O)$_2$R'; —S(=O)OR'; —S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five $R_2$ groups; heteroaryl optionally substituted with one, two, three, four or five groups independently selected from $R_2$ groups; and cycloalkyl optionally substituted with one, two, three, four or five groups independently selected from $R_2$ groups; each $R_1$ group is independently selected from the group consisting of hydroxyl, halo, $C_1$-$C_6$ alkoxy, —NR'R''; —S(=O)$_2$R'; —S(=O)OR'; —S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); —OC(=O)NR'R''; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; each $R_2$ group is independently selected from the group consisting of $C_1$-$C_6$ alkyl, $C_{2-6}$ alkyenyl, $C_2$-$C_6$ alkynyl, hydroxyl, halo, $C_1$-$C_6$ alkoxy, —NR'R''; —S(=O)$_2$R'; —S(=O)OR'; —S(=O)R'; —C(=O)OR'; —CN; —C(=O)R'; —SR', —N=N$^+$=N$^-$; —NO$_2$, —OSO$_2$R'; —C(=O)OR'; —O(=S)SR'; —P(=O)(OR')$_2$; —OP(=O)(OR')$_2$; —P(=O)(OR')R''; —N=R'R''; —NR'P(OR'')(OR'''); OC(=O)NR'R''; aryl optionally substituted with one, two, three, four or five R' groups; heteroaryl optionally substituted with one, two, three, four or five groups independently selected from R' groups; and cycloalkyl optionally substituted with one, two, three, four or five groups independently selected from R' groups; and wherein each R', R'', and R''' are independently selected from the group consisting of H, $C_1$-$C_6$ alkyl, and aryl. Examples of compounds of Formula (I) include α-, β- and γ-cyclodextrins.

As used herein, the term "alkyl" refers to a straight or branched chain alkyl radical. Examples include, but are not limited, to methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. Each alkyl group may be optionally substituted with one, two or three substituents such as a halo, cycloalkyl, aryl, alkenyl or alkoxy group.

As used herein, the term "lower alkenyl" refers to a straight or branched hydrocarbon radical having one or two double bonds and includes, for example, ethenyl, propenyl, 1-but-3-enyl, 1-pent-3-enyl, and 1-hex-5-enyl. The alkenyl group can also be optionally mono-, di-, or trisubstituted with, for example, halo, aryl, cycloalkyl or alkoxy.

As used herein, the term "alkynyl" refers to a straight or branched hydrocarbon radical having one or two triple bonds and includes, for example, propynyl and 1-but-3-ynyl. The alkynyl group can also be optionally mono-, di-, or trisubstituted with, for example, halo, aryl, cycloalkyl or alkoxy.

As used herein, the term "alkoxy" refers to an —O—alkyl group in which the alkyl is as defined above.

As used herein, the term "halo" or "halogen" refers to a halogen radical of fluorine, chlorine, bromine, or iodine.

As used herein, the term "aryl" refers to an aromatic carbocyclic radical having a single ring (e.g. phenyl), multiple rings (e.g. biphenyl), or multiple fused rings in which at least one is aromatic (e.g. 1,2,3,4-tetrahydronaphthyl).

As used herein, the term "heteroaryl" refers to one aromatic ring or multiple fused aromatic ring systems of 5-, 6- or 7-membered rings containing at least one and up to four heteroatoms (e.g., nitrogen, oxygen or sulfur). Examples include, but are not limited to, furanyl, thienyl, pyridinyl, pyrimidinyl, benzimidazolyl and benzoxazolyl.

As used herein, the term "cycloalkyl" refers to a carbocylic radical having a single ring (e.g., cyclohexyl), multiple rings (e.g., bicyclohexyl) or multiple fused rings (e.g., decahydronaphthalenyl). In addition, the cycloalkyl group may have one or more double bonds.

Without wishing to be bound by theory, it is believed that the CD-MOFs described herein can adsorb the active agent molecules in the compositions onto its pores and thereby stabilize the release rate of the active agent. Unexpectedly, the inventors discovered that adding a CD-MOF into a composition containing an active agent can maintain the release of the active agent for a longer period of time and can increase the total release amount of the active agent compared to a similar composition without any CD-MOF or a similar composition contain the same amount of a corresponding CD used to prepare the CD-MOF. As a result, such a composition can exhibit significantly improved release profile (e.g., by increasing the average release rate, the effective release duration, and/or the total release amount of the active agent). In addition, it is believed that, when CD-MOFs are loaded with active agent molecules, CD-MOFs can act as reservoirs to store and steadily release the active agent molecules. This is different from conventional cyclodextrins, where their utility is primarily complex formation between the host cyclodextrin and guest molecules. Specifically, when cyclodextrins form complexes with guest molecules, the guest molecules are not steadily released under ambient environment, but rather trapped indefinitely within the cyclodextrin cavities and only released by external force such as water and heat.

In general, the compositions described herein can include a suitable amount of one or more of the CD-MOFs depending on the intended uses of the compositions. In some embodiments, the CD-MOFs can range from at least about 0.2 wt % (e.g., at least about 0.5 wt %, or at least about 1 wt %, at least about 2 wt %, at least about 3 wt %, at least about 4 wt %, at least about 5 wt %, at least about 6 wt %, at least about 7 wt %, at least about 8 wt %, or at least about 9 wt %) to at most about 95 wt % (e.g., at most about 90 wt %, at most about 80 wt %, at most about 70 wt %, at most about 60 wt %, at most about 50 wt %, at most about 40 wt %, at most about 30 wt %, at most about 20 wt %, at most about 10 wt %, at most about 9.5 wt %, at most about 8.5 wt %, at most about 7.5 wt %, at most about 6.5 wt %, at most about 5.5 wt %, at most about 4.5 wt %, at most about 3.5 wt %, at most about 2.5 wt %, or at most about 1.5 wt %) of the compositions described herein. In some embodiments, the compositions can have a relatively high percentage (e.g., from about 10 wt % to about 95 wt %) of the CD-MOFs when the compositions contain a small amount of a carrier (e.g., a solvent) or contain no carrier at all.

In general, the CD-MOFs in the compositions described herein are in the form of particles (e.g., crystal particles) and can have any suitable particle size depending on the intended uses of the compositions. In some embodiments, the CD-MOFs can have an average particle size of at least about 10 nm (e.g., at least about 20 nm, at least about 50 nm, at least about 100 nm, at least about 200 nm, at least about 500 nm, or at least about 1 μm) to at most about 1 cm (e.g., at most about 5 mm, a most about 1 mm, at most about 500 μm, at most about 100 μm, at most about 50 μm, at most about 10 μm, at most about 5 μm, or at most about 1 μm). It is believed that when the CD-MOFs have an average particle size from about 10 nm to about 1 μm, the compositions containing such CD-MOFs can be a suspension (e.g., a dispersion or a colloid). In addition, it is believed that when the CD-MOFs have an average particle size from about 1 μm to about 1 cm, the compositions containing such CD-MOFs can be an emulsion (such as a lotion, a cream, or an ointment) or a gel.

In some embodiments, the compositions described herein can optionally contain a suitable carrier, such as one or more solvents, one or more oils, or a combination thereof. The solvents that can be used in the compositions can include organic solvents, aqueous solvents (e.g., water or an aqueous solution), or a combination thereof. Exemplary organic solvents include a hydrocarbon solvent (e.g., a mineral oil), an alcohol (e.g., ethanol, isopropanol, or propylene glycol), a ketone (e.g., acetone), an ester (e.g., ethyl acetate). Exemplary aqueous solvents include water and a mixture of water and one or more other solvents (e.g., an alcohol). Exemplary oils include fractionated coconut oil, jojoba oil, grapeseed oil, and sunflower oil. In some embodiments, the compositions can include at least about 0 wt % (e.g., at least about 5 wt %, at least about 10 wt %, at least about 20 wt %, at least about 30 wt %, at least about 40 wt %, at least about 50 wt %, at least about 55 wt %, at least about 60 wt %, at least about 65 wt %, at least about 70 wt %, at least about 75 wt %, at least about 80 wt %, at least about 85 wt %, or at least about 90 wt %) and/or at most about 99.7 wt % (e.g., at most about 99 wt %, at most about wt %, at most about 95 wt %, at most about 90 wt %, at most about 85 wt %, at most about 80 wt %, or at most about 75 wt %) of the carrier. In some embodiments, the compositions do not contain any carrier. In such embodiments, the compositions can contain an active agent in a CD-MOF in a solid form, such as a powder.

In some embodiments, it can be desirable for the carrier to be an oil solvent (e.g., about 100 percent oil, or in some embodiments, consisting essentially of oil with only trace, e.g., less than 1% other solvents present). While not limiting the scope of the disclosure by theoretical considerations, it is thought that an oil solvent can surround the CD-MOF complex and thereby stabilize the complex, e.g., by occluding water molecules from penetrating into the complex until the composition ready to be used. Alternatively, in some embodiments the carrier can be an organic solvent (e.g., about 100 percent organic solvent, or in some embodiments, consist essentially of organic solvent with only trace, e.g., less than 1% other solvents present). In some embodiments, the carrier can be an ester, an alcohol, a ketone, an ether, or a hydrocarbon solvent.

Alternatively, in some embodiments, the carrier can be an aqueous solvent (e.g., about 100 percent aqueous solvent, or in some embodiments, consist essentially of aqueous solvent with only trace, e.g., less than 1% other solvents present). In some embodiments the carrier can be an aqueous solvent, and the composition of the active agent and the CD-MOF (the CD-MOF complex) can be at least about 10 wt % to at most about 90 wt % of the carrier.

Having an organic solvent or aqueous solvent carrier being the carrier or included in the carrier provide the composition with a more desirable non-greasy feeling when applied to a subject's skin. Additionally, an organic solvent or aqueous solvent may advantageously solubilize certain active agents.

Alternatively in some embodiments, the carrier can be a mixture of an oil solvent and an aqueous solvent or a mixture of an oil solvent and an organic solvent or a mixture of an organic solvent and an aqueous solvent or a mixture of an oil solvent, an aqueous solvent and an organic solvent. For instance, in some embodiments, the carrier can be a mixture of an oil solvent and an aqueous solvent having a ratio (e.g., oil:water ratio) in a range from about 10:90 to about 90:10, and in some embodiments about 20:80 to about 80:20, and in some embodiments, about 20:80 to 50:50. For instance, in some embodiments, the carrier can be a mixture of an organic solvent and an aqueous solvent having a ratio (organic:water ratio) in a range from about 90:10 to about 50:50, and in some embodiments about 90:810 to about 80:20.

It can be desirable to have some oil present in the carrier because it is thought that the oil can surround to CD-MOF complex and thereby stabilize the complex as described above. However, it can also be desirable to have some aqueous solvent or organic solvent present in the carrier to solubilize active agent and/or provide the composition the more desirable non-greasy feeling.

In some embodiments, the compositions described herein can include one or more optional additives, such as penetration enhancers, fixatives, emulsifiers (such as surfactants), antioxidants, preservatives, humectants, oils, thickening agents, and silicones.

Exemplary penetration enhancers include glycols (e.g., propylene glycol), sulphoxides (e.g., dimethylsulphoxide), bile salts and derivatives (e.g., sodium glyacolate or sodium deoxycholate), fatty acids and derivatives (e.g., oleic acid or caprylic acid), chelating agents (e.g., ethylenediaminetetraacetic acid), azones (e.g., laurocapram), pyrrolidones (e.g., 2-pyrrolidone), alcohols (e.g., ethanol, decanol, benzyl alcohol, and 1,2,6-hexapetriol), terpenes, diisopropyl adipate, dimethyl isosorbide, and a combination thereof. In some embodiments, the compositions described herein can include at least about 0.1 wt % (e.g., at least about 0.5 wt %, at least about 1 wt %, at least about 2 wt %, at least about 3 wt %, at least about 4 wt %, or at least about 5 wt %) and/or at most about 10 wt % (e.g., at most about 9 wt %, at most about 8 wt %, at most about 7 wt %, at most about 6 wt %, or at most about 5 wt %) of the penetration enhancer. In some embodiments, the compositions do not contain any penetration enhancer.

In some embodiments, the compositions described herein can include one or more emulsifiers, such as ionic emulsifiers or non-ionic emulsifiers. For example, the emulsifiers can include lecithin, beeswax, borax, propylene glycol stearate, sorbitan tristearate, sorbitan monostearate, emulsifying wax, cetearyl alcohol, polysorbate 20, polysorbate 60, cetearyl alcohol, palm stearic, and dicetyl phosphate. In some embodiments, the composition can include at least about 0.01 wt % (e.g., at least about 0.1 wt %, at least about 0.5 wt %, at least about 1 wt %) to at most about 5 wt % (e.g., at most about 1 wt %, at most about 0.5 wt %, or at most about 0.1 wt %) of the emulsifier. Without wishing to be bound by theory, it is believed that adding an emulsifier to the compositions can facilitate formation of emulsions. In some embodiments, the compositions described herein do not contain any emulsifier.

In some embodiments, the compositions described herein can be topical compositions. For example, the compositions described herein can be suspensions (e.g., lotions, dispersions, or colloids), emulsions (e.g., lotions, creams, ointments), gels, aerosols, sprays, or a combination thereof (e.g., pastes). In some embodiments, the compositions can be applied onto adhesive patches to form transdermal patches.

The compositions described herein can be prepared by methods known in the art. For example, a composition can be prepared by pre-loading an active agent onto a CD-MOF in a solvent to form a mixture (e.g., by mixing an active agent with a CD-MOF in a solvent), followed by adding any optional components (e.g., optional carriers or additives) to the above mixture. As another example, a composition can be prepared by first mixing an active agent with any optional components in a solvent, followed by adding a CD-MOF into the mixture. As a further example, a composition can be prepared by first mixing a CD-MOF with any optional components in a solvent, followed by adding an active agent into the mixture.

In general, the compositions described herein can be used in any suitable cosmetic applications (such as perfumes, colognes, body sprays, hair sprays, body lotions (e.g., hand lotions), moisturizers, aftershave, deodorant, skin care products, and makeup products) and non-cosmetic applications (e.g., detergents, fabric softeners, dryer sheets, air fresheners, carpet fresheners, aromatherapy, hand sanitizers, shower gels, shampoos, liquid soaps, bar soaps, bath salts, and therapeutic or medicinal products (such as ointments, creams, syrups (e.g., cough suppression syrups), aerosols, sprays, and transdermal patches (e.g., those used to ease muscle aches, joint pain, or headaches)).

This disclosure also features methods of using the compositions described above. In some embodiments, the methods can include at least the following steps: (1) treating a subject's skin with at least one of the compositions described above to form a treated area on the skin; and (2) applying water to the treated area. Without wishing to be bound by theory, it is believed that applying water to the composition on the treated area of the skin can facilitate the release of the active agent from the composition (e.g., by dissolving the active agent CD-MOF complex in water) and facilitate diffusion of the active agent through the skin.

In some embodiments, the methods of using the compositions described above can include at least the following steps: (1) treating a subject's skin with at least one of the compositions described above to form a treated area on the skin; and (2) applying force to the treated area. For example, the step of applying force to the treated area can include rubbing or scrubbing the composition on the treated area. Without wishing to be bound by theory, it is believed that applying force to the composition on the treated area of the skin facilitate the release of the active agent from the composition (e.g., by breaking up the active agent CD-MOF complex such that the active agent can be released from the complex) and facilitate diffusion of the active agent through the skin.

In some embodiments, without wishing to be bound by theory, it is believed that the compositions described herein can have a longer release duration or more extended release of the active agent than similar compositions without any CD-MOF or similar compositions containing the same amount of the corresponding CD, thereby resulting in a longer cosmetic or therapeutic effect. For example, when a composition described herein is applied to a subject's skin, the composition can release a first amount of the active agent at 24 hours after application (which can be lower than the total amount of the active agent in the composition) and the time to release 50 wt % of the first amount is at least about 1 hour (e.g., at least about 2 hours, at least about 3 hours, at least about 4 hours, at least about 5 hours, at least about 6 hours, at least about 8 hours, or at least about 10 hours) and/or at most about 10 hours (e.g., at most about 9 hours, at most about 8 hours, at most about 7 hours, at most about 6 hours, at most about 5 hours, at most about 4 hours, at most about 3 hours, or at most about 2 hours). By contrast, similar compositions without any CD-MOF or similar compositions containing the same amount of the corresponding CD typically release 50 wt % of the total amount of the active agent released at 24 hours (which can be lower than the total amount of the active agent in the compositions) in a relatively short period of time (e.g., less than one hour).

In some embodiments, without wishing to be bound by theory, it is believed that the compositions described herein can release a larger amount of the active agent at 24 hours after application than similar compositions without any CD-MOF or similar compositions containing the same amount of the corresponding CD, thereby resulting in a stronger cosmetic or therapeutic effect. For example, when the composition described herein is applied to a subject's skin, at 24 hours after application, the composition can release at least about 50 wt % (e.g., at least about 55 wt %, at least about 60 wt %, at least about 65 wt %, at least about 70 wt %, at least about 75 wt %, or at least about 80 wt %) and/or at most about 99 wt % (e.g., at most about 95 wt %, at most about 90 wt %, at most about 85 wt %, at most about 80 wt %, at most about 75 wt %, or at most about 70 wt %) of the total amount of the active agent in the composition. By contrast, at 24 hours after application, similar compositions without any CD-MOF or similar compositions containing the same amount of the corresponding CD typically release a relatively small amount of the active agent (e.g., less than about 50 wt % of the total amount of the active agent in the compositions).

The following examples are illustrative and not intended to be limiting.

CD-MOF crystals were prepared following a similar procedure as described in U.S. Pat. No. 9,085,460. Specifically, CD-MOF crystals were grown through vapor diffusion of methanol into an aqueous solution of gamma-cyclodextrin and potassium hydroxide. The crystals were left to grow for a period of about 1 to 2 weeks, after which they were collected, filtered, washed with methanol, and then evacuated in a vacuum chamber at room temperature to approximately 10-3 Torr for 24 hours. The CD-MOF crystals were then used in the following experiments without further purification.

To measure the cumulative release profile of the topical formulations containing a CD-MOF, a vertical diffusion cell test system was employed. The Franz type cell had a fixed 7 mL volume receptor chamber with a magnetic stirrer, water jacket for temperature consistency, a synthetic membrane separating the sealed top donor chamber from the bottom receptor chamber, and a clamp assembly that held the receptor chamber, membrane, and donor chamber in place for even cell-top pressure. The amount of an active agent that traversed from the donor chamber into a medium in the receptor chamber through the synthetic membrane was sampled over time to obtain the diffusion profile of the active agent to characterize its skin delivery efficiency. The receptor medium was de-ionized water. The donor chamber included the test sample, but did not include any medium. Diffusion cell temperature was controlled by a water bath circulator set to 32.5° C. Water from the temperature-controlled bath circulator flowed through the water jacket of the diffusion cell as well as through a jacketed beaker containing a replacement medium. The procedure to take samples from the receptor medium was to use a precision syringe to inject the replacement medium at the bottom of the cell through a bottom port that pushes the sample within the cell out the top port of the cell. UV-VIS spectroscopy was used for 1 mL aliquots taken from the receptor medium to determine the amount of the active agent that traversed from the donor chamber through the membrane into the receptor medium. Samples were taken at 10 minutes, 30 minutes, 1 hour, 1.5 hours, 2 hours, and then every 2 hours until 30 hours elapsed since the formulation sample came into contact with the membrane.

In this example, a commonly-used cosmetic and therapeutic agent, salicylic acid, was the compound of interest whose diffusion profile through a synthetic membrane was measured for three different types of formulation samples. The first formulation sample was salicylic acid loaded into 30 mg CD-MOF dispersed in 1 mL ethanol. The second formulation sample was salicylic acid alone dissolved in 1 mL ethanol. The third formulation sample was salicylic acid loaded into 30 mg γCD dispersed in 1 mL ethanol. In these formulation samples, CD-MOF was loaded with salicylic acid by soaking it in a salicylic acid ethanol solution. The mixture was then dried to evaporate the ethanol, leaving a dry CD-MOF powder loaded with salicylic acid. The dry CD-MOF powder was then dispersed in 1 mL ethanol.

Without wishing to be bound by theory, it is believed that when salicylic acid is loaded into the CD-MOF samples, the drug molecules diffuse and are positioned within the internal pore spaces of the CD-MOF crystals to form an agent-CD-MOF complex. The agent-CD-MOF complex can then be mixed in a formulation such as a cream, lotion, gel, with a water content that does not decompose the agent-CD-MOF complex. In such a formulation, the agent-CD-MOF complex can be relatively stable. Upon topical application, mixing the agent-CD-MOF complex with water and/or abrasion of the agent-CD-MOF complex (e.g., by scrubbing or physical application) can cause the agent-CD-MOF complex to break into smaller particles, and even decompose into agent-cyclodextrin complexes, individual agent, and cyclodextrin molecules.

The results obtained from the above vertical diffusion cell test are summarized in FIGS. 1-5. In these figures, x-axis represents the time elapsed since a formulation sample came into contact with the membrane, and y-axis represents the total amount of salicylic acid that crossed the membrane and released into the receptor medium within a certain time.

Figure 1:
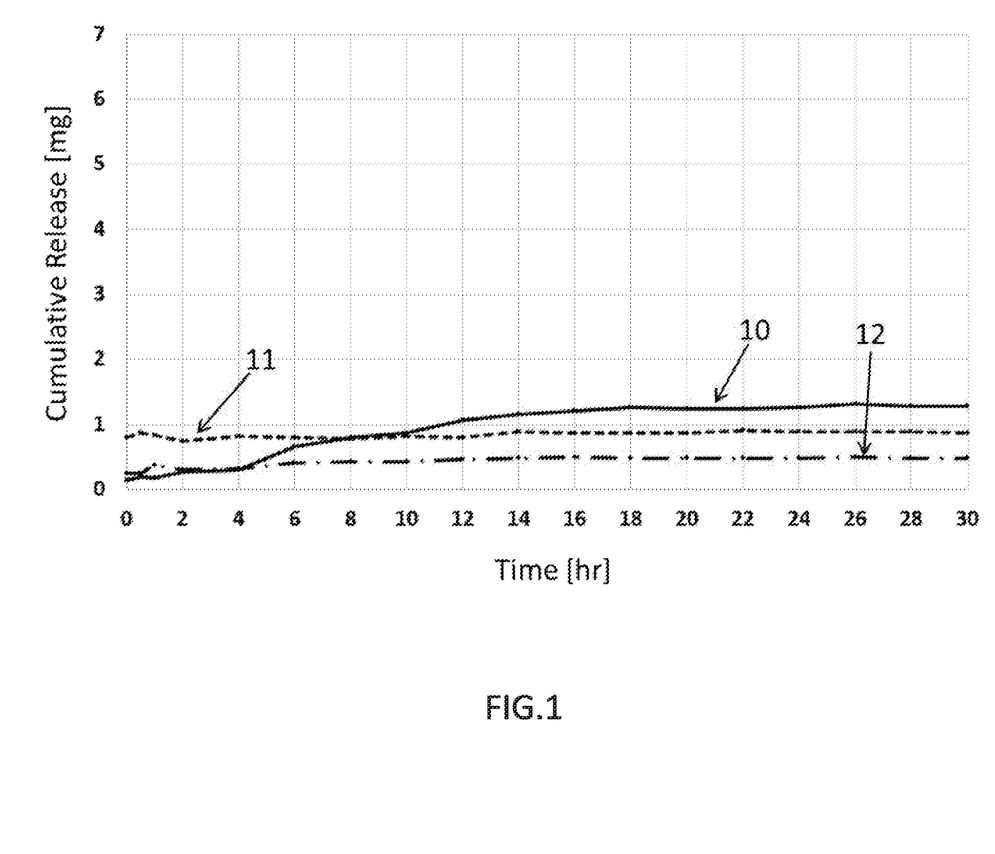
FIG. 1 is a graph including curves showing (a) the cumulative release profile of a composition containing 2 mg of salicylic acid loaded in 30 mg of a $\gamma$CD-MOF dispersed in 1 mL ethanol (10), (b) the cumulative release profile of a composition containing 2 mg of salicylic acid dissolved in 1 mL ethanol (11), and (c) the cumulative release profile of a composition containing 2 mg of salicylic acid loaded in 30 mg of γCD dispersed in 1 mL ethanol (12).

FIG. 1 is a graph including curves showing (a) the cumulative release profile of a composition containing 2 mg of salicylic acid loaded in 30 mg of a γCD-MOF dispersed in 1 mL ethanol (10), (b) the cumulative release profile of a composition containing 2 mg of salicylic acid dissolved in 1 mL ethanol (11), and (c) the cumulative release profile of a composition containing 2 mg of salicylic acid loaded in 30 mg of γCD dispersed in 1 mL ethanol (12).

As shown in FIG. 1, in both the sample containing salicylic acid only (11) and the sample containing salicylic acid mixed with gamma-cyclodextrin (12), most of the total amount of salicylic acid released during the span of 30 hours crossed the membrane within the first few minutes. The rest of the diffusion profile after this point until 30 hours was reached is generally flat, suggesting that no significant amount of salicylic acid crossed the membrane after the initial few minutes. However, as shown in FIG. 1, for the sample containing CD-MOF (10), salicylic acid steadily crossed the membrane at an average release rate of about 0.06 mg per hour until at about 16 hours, where the release rate reduced and the cumulate release profile became flattened. It is believed that the salicylic acid was slowly diffusing out of the CD-MOF matrix before it reached the membrane. Therefore, the CD-MOF increased the effective release duration of salicylic acid by more than 16 times. Without wishing to be bound by theory, it is also believed that since the membrane was soaked in water (from the receptor medium) prior to adding the samples, the water present on the donor side can break down and dissolve a part of the salicylic acid CD-MOF complex, and continue to do so over time as more water diffused from the receptor side to the donor side.

Figure 2:
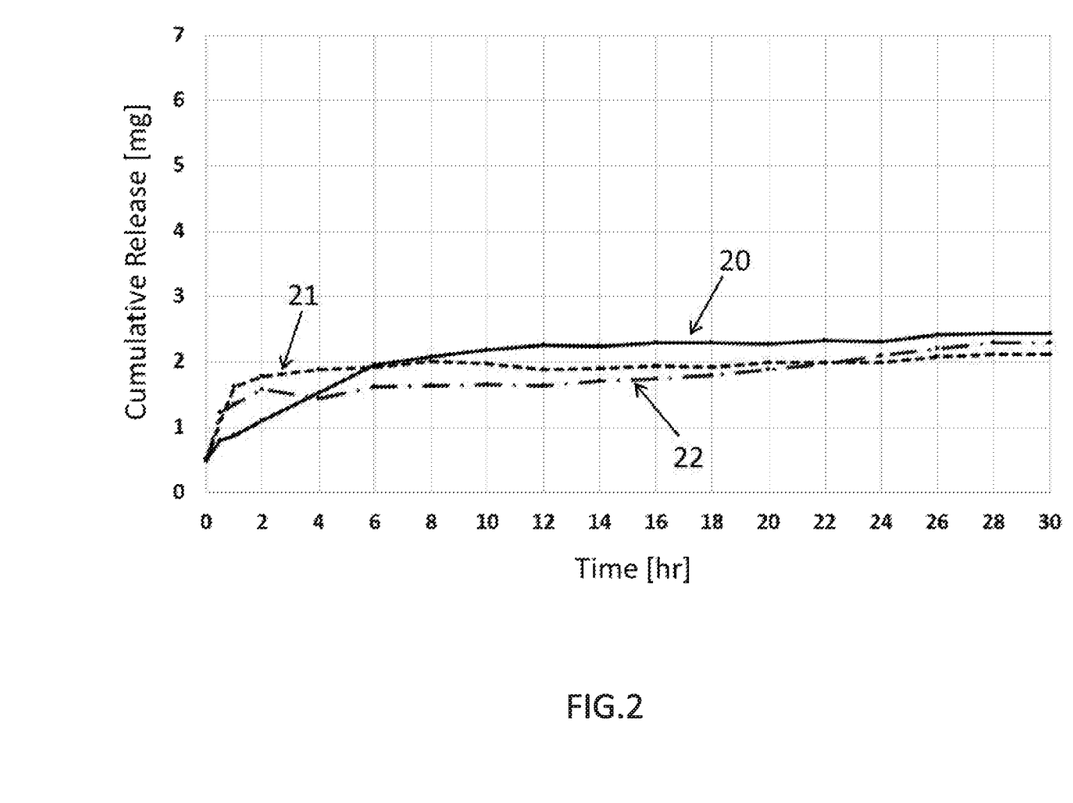
FIG. 2 is a graph including curves showing (a) the cumulative release profile of a composition containing 4 mg of salicylic acid loaded in 30 mg of a γCD-MOF dispersed in 1 mL ethanol (20), (b) the cumulative release profile of a composition containing 4 mg of salicylic acid dissolved in 1 mL ethanol (21), and (c) the cumulative release profile of a composition containing 4 mg of salicylic acid loaded in 30 mg of γCD dispersed in 1 mL ethanol (22).

FIG. 2 is a graph including curves showing (a) the cumulative release profile of a composition containing 4 mg of salicylic acid loaded in 30 mg of a γCD-MOF dispersed in 1 mL ethanol (20), (b) the cumulative release profile of a composition containing 4 mg of salicylic acid dissolved in 1 mL ethanol (21), and (c) the cumulative release profile of a composition containing 4 mg of salicylic acid loaded in 30 mg of γCD dispersed in 1 mL ethanol (22).

As shown in FIG. 2, the total release amounts for the three tested samples were approximately between 2 mg and 2.5 mg after a duration of 30 hours. Both the sample containing salicylic acid only (21) and the sample containing salicylic acid and gamma-cyclodextrin (22) released 50% of the total released amount (i.e., 2-2.5 mg) in less than one hour and released most of the total released amount in less than two hours. By contrast, the sample containing salicylic acid and CD-MOF (20) showed a steady release rate of approximately 0.14 mg/hour for the first 12 hours. This is an increase of at least about 6 times in effective duration of steady release compared to reference samples (21) and (22).

Figure 3:
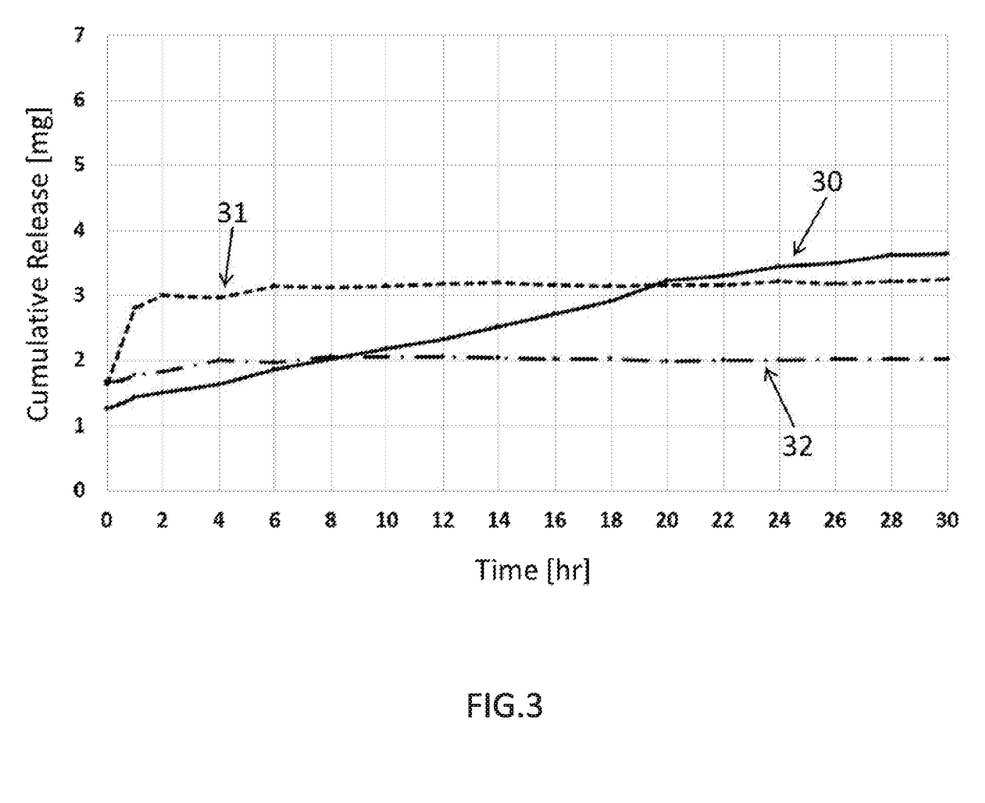
FIG. 3 is a graph including curves showing (a) the cumulative release profile of a composition containing 6 mg of salicylic acid loaded in 30 mg of a γCD-MOF dispersed in 1 mL ethanol (30), (b) the cumulative release profile of a composition containing 6 mg of salicylic acid dissolved in 1 mL ethanol (31), and (c) the cumulative release profile of a composition containing 6 mg of salicylic acid loaded in 30 mg of γCD dispersed in 1 mL ethanol (32)

FIG. 3 is a graph including curves showing (a) the cumulative release profile of a composition containing 6 mg of salicylic acid loaded in 30 mg of a γCD-MOF dispersed in 1 mL ethanol (30), (b) the cumulative release profile of a composition containing 6 mg of salicylic acid dissolved in 1 mL ethanol (31), and (c) the cumulative release profile of a composition containing 6 mg of salicylic acid loaded in 30 mg of γCD dispersed in 1 mL ethanol (32).

As shown in FIG. 3, reference sample (31) contained 6 mg salicylic acid and had a total cumulative release of about 3.3 mg after 30 hours. Of the 3.3 mg total released amount, about 2.5 mg was released in the first hour and about 3 mg was released within the first 2 hours. Reference sample (32) contained 6 mg salicylic acid mixed with 30 mg gamma-cyclodextrin and had about a total cumulative release of 2 mg after 30 hours. Of the 2 mg total released amount, about 1.5 mg was released in the first hour and almost the entire total released amount was released within the first 4 hours. Remarkably, the CD-MOF sample (30) contained 6 mg salicylic acid and had a total cumulative release of about 3.6 mg after 30 hours. In addition, the CD-MOF sample (30) had an approximately constant release rate of 0.08 mg/hour for the entire 30-hour duration. This is an increase of at least 15 times and 7.5 times increase in effective steady release duration compared to reference samples (31) and (32), respectively.

Figure 4:
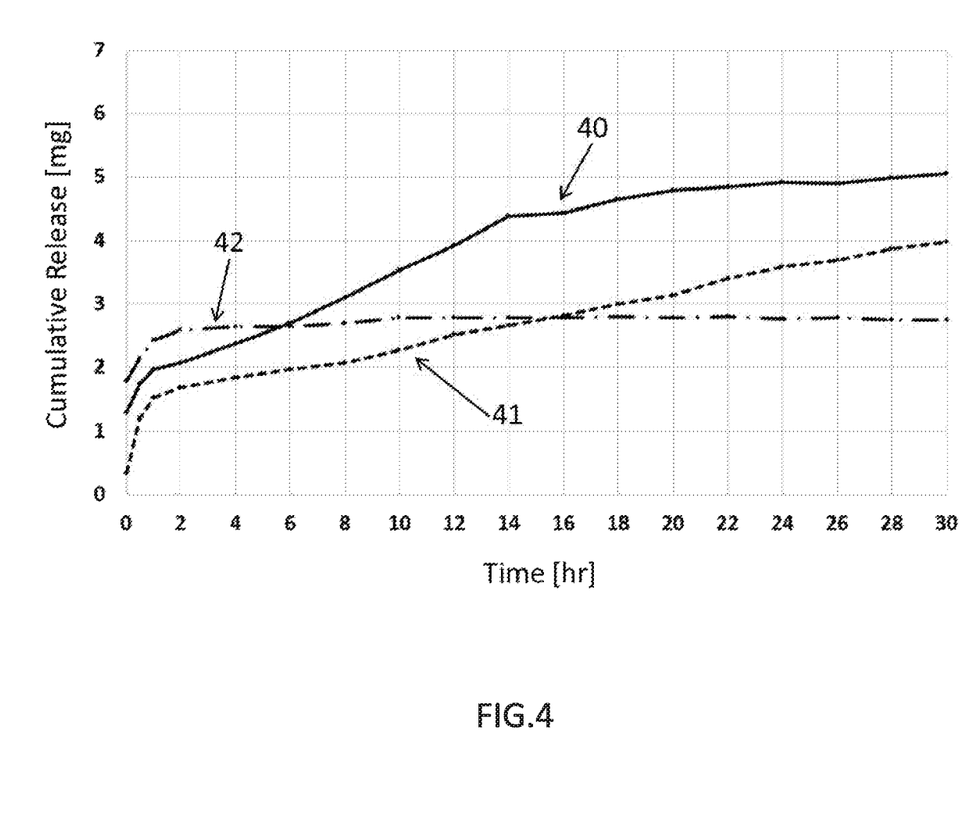
FIG. 4 is a graph including curves showing (a) the cumulative release profile of a composition containing 8 mg of salicylic acid loaded in 30 mg of a γCD-MOF dispersed in 1 mL ethanol (40), (b) the cumulative release profile of a composition containing 8 mg of salicylic acid dissolved in 1 mL ethanol (41), and (c) the cumulative release profile of a composition containing 8 mg of salicylic acid loaded in 30 mg of γCD dispersed in 1 mL ethanol (42)

FIG. 4 is a graph including curves showing (a) the cumulative release profile of a composition containing 8 mg of salicylic acid loaded in 30 mg of a γCD-MOF dispersed in 1 mL ethanol (40), (b) the cumulative release profile of a composition containing 8 mg of salicylic acid dissolved in 1 mL ethanol (41), and (c) the cumulative release profile of a composition containing 8 mg of salicylic acid loaded in 30 mg of γCD dispersed in 1 mL ethanol (42).

As shown in FIG. 4, reference sample (41) contained 8 mg salicylic acid and had a total cumulative release of about 4 mg after 30 hours. Of the 4 mg total released amount, about 1.5 mg was released in the first hour. Reference sample (42) contained 8 mg salicylic acid mixed with 30 mg gamma-cyclodextrin and had about a total cumulative release of 2.8 mg after 30 hours. Of the 2.8 mg total released amount, about 2.4 mg was released in the first hour. By contrast, the CD-MOF sample (40) contained 8 mg salicylic acid and had a total cumulative release of about 5 mg after 30 hours. Although reference sample (41) had a similar shape in release profile to the CD-MOF sample (40), the average release rate for the CD-MOF sample (40) (i.e., 0.11 mg/hour) was higher than that of reference sample (41) (i.e., 0.09 mg/hour).

Figure 5:
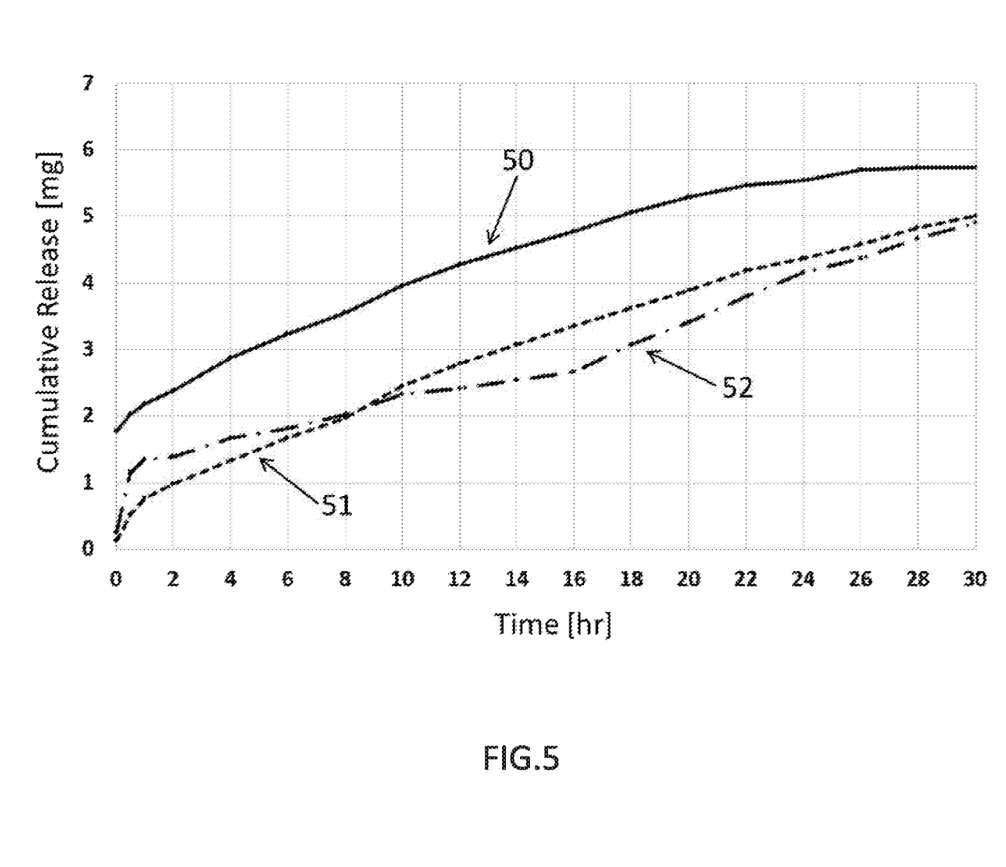
FIG. 5 is a graph including curves showing (a) the cumulative release profile of a composition containing 10 mg of salicylic acid loaded in 30 mg of a γCD-MOF dispersed in 1 mL ethanol (50), (b) the cumulative release profile of a composition containing 10 mg of salicylic acid dissolved in 1 mL ethanol (51), and (c) the cumulative release profile of a composition containing 10 mg of salicylic acid loaded in 30 mg of γCD dispersed in 1 mL ethanol (52)

FIG. 5 is a graph including curves showing (a) the cumulative release profile of a composition containing 10 mg of salicylic acid loaded in 30 mg of a γCD-MOF dispersed in 1 mL ethanol (50), (b) the cumulative release profile of a composition containing 10 mg of salicylic acid dissolved in 1 mL ethanol (51), and (c) the cumulative release profile of a composition containing 10 mg of salicylic acid loaded in 30 mg of γCD dispersed in 1 mL ethanol (52).

As shown in FIG. 5, reference sample (51) contained 10 mg salicylic acid and had a total cumulative release of about 5 mg after 30 hours. Of the 5 mg total released amount, about 0.7 mg was released in the first hour. Reference sample (52) contained 10 mg salicylic acid mixed with 30 mg gamma-cyclodextrin and had about a total cumulative release of 5 mg after 30 hours. Of the 5 mg total released amount, about 1.3 mg was released in the first hour. By contrast, the CD-MOF sample (40) contained 10 mg salicylic acid and had a total cumulative release of about 5.7 mg after 30 hours. In the above tests, the amount of the CD-MOF was kept constant at 30 mg. Thus, when the amount of salicylic acid loaded into the CD-MOF increased, the loading ratio increased. Without wishing to be bound by theory, it is hypothesized that, as the loading ratio increases to a certain degree, the differences between CD-MOF samples and reference samples may be reduced.

Figure 6:
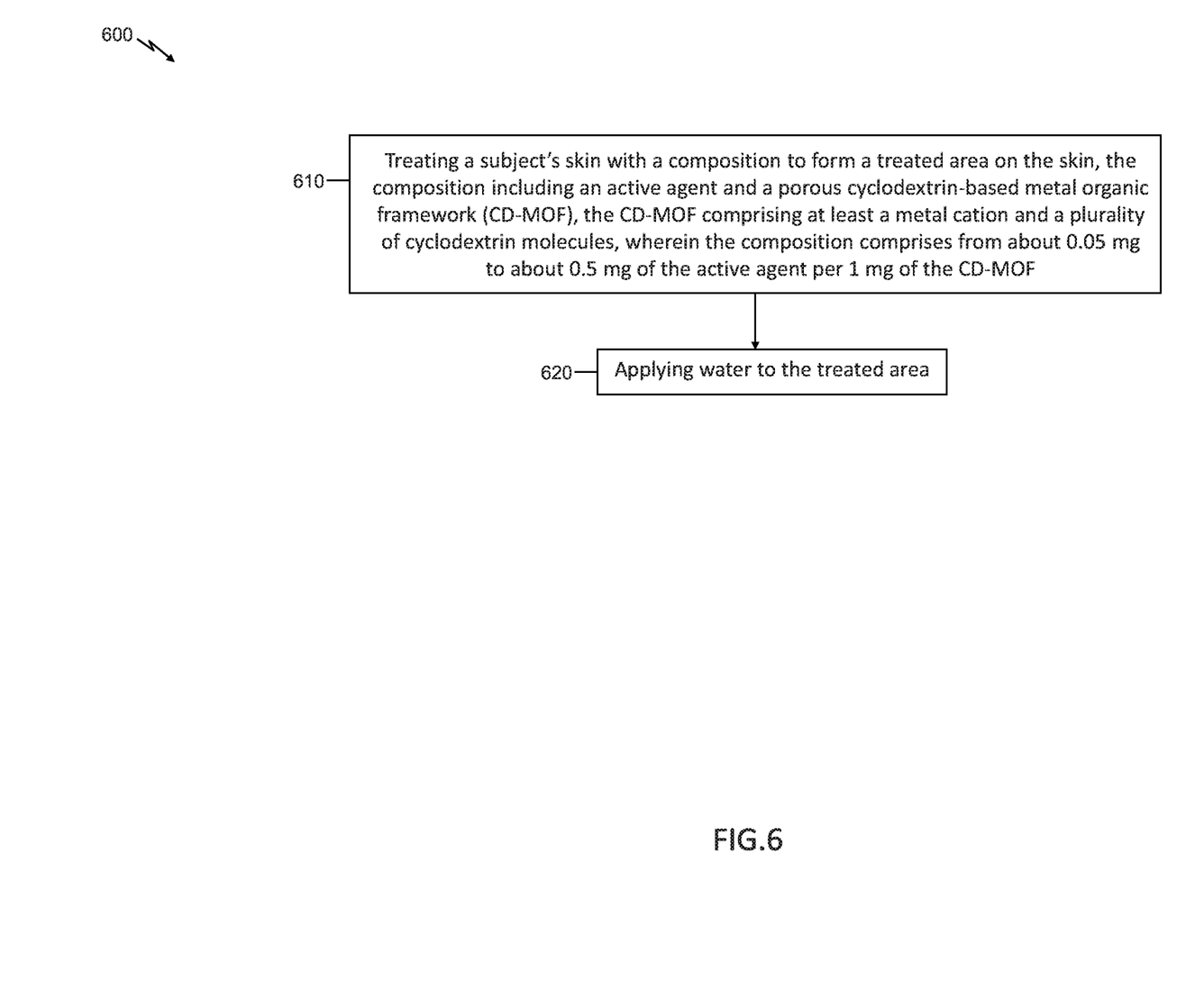
FIG. 6 presents a flow diagram of an example method of using a composition, such as any of the compositions described herein.

FIG. 6 presents a flow diagram of an example method 600 of using a composition, such as any of the compositions described herein. The method 600 can include treating a subject's (e.g., a human or animal subject) skin with a composition to form a treated area on the skin (step 610). The composition can include an active agent and a porous cyclodextrin-based metal organic framework (CD-MOF) (e.g., a CD-MOF complex), the CD-MOF comprising at least a metal cation and a plurality of cyclodextrin molecules, wherein the composition comprises from about 0.05 mg to about 0.5 mg of the active agent per 1 mg of the CD-MOF, The method 600 can also include applying water to the treated area (step 620).

The amount of water applied to the treated area of skin in step 620 is selected to facilitate the chemical release of the active agent from the CD-MOF complex. For example, in some embodiments, the amount of liquid water added to the composition can be a weight that is equal to or greater than the weight of the composition applied to the skin as part of step 610. For example, in some embodiments, a ratio of the weight of the composition applied to the treated area in step 810 to the weight of water applied in step 620 can be at least about 1:1 in some embodiments and at least about 1:2 or at least about 1:3 in some embodiments.

Figure 7:
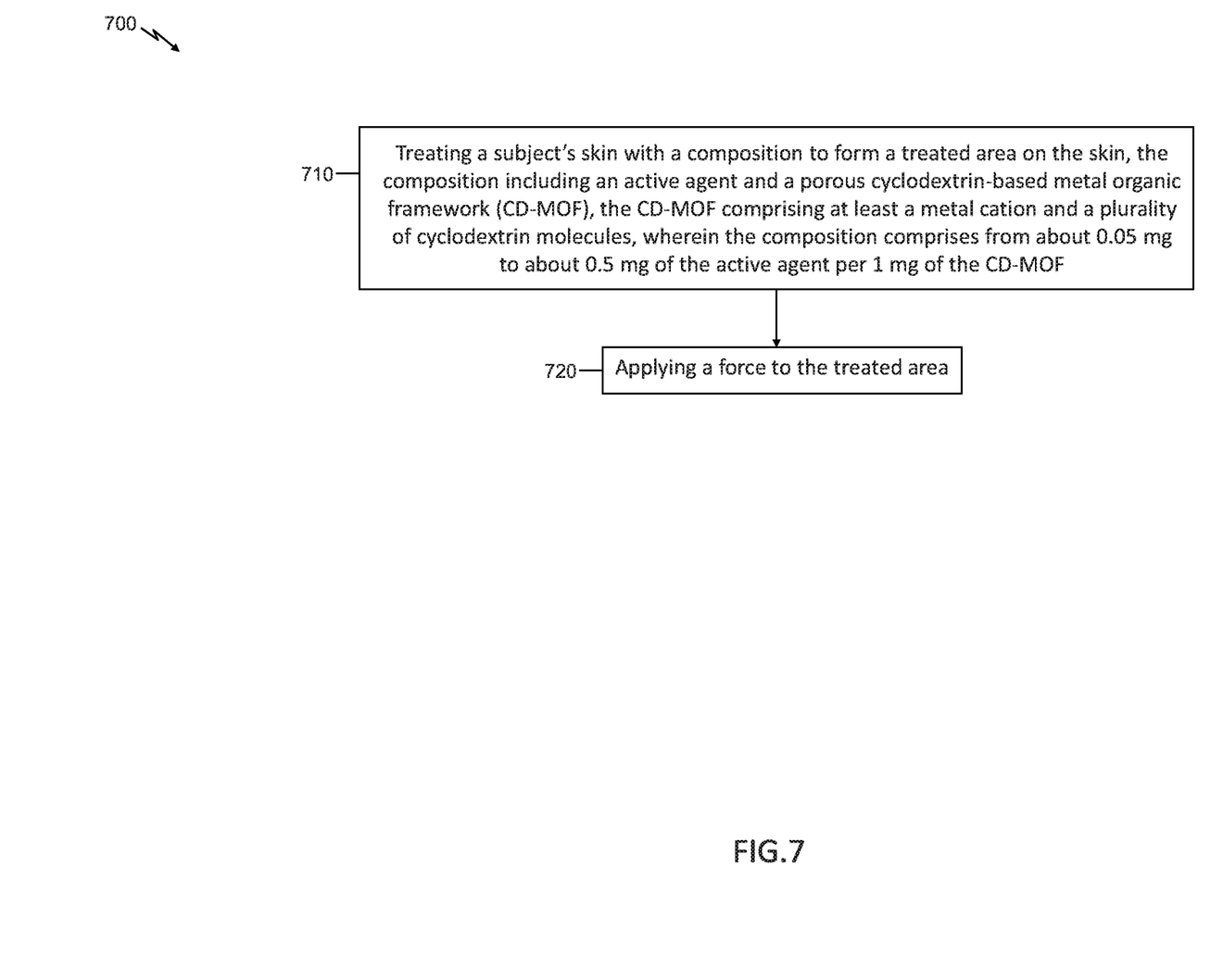
FIG. 7 presents a flow diagram of another example method of using a composition, such as any of the compositions described herein.

FIG. 7 presents a flow diagram of another example method 700 of using a composition, such as any of the compositions described herein.

The method 700 can include treating a subject's skin with a composition to form a treated area on the skin (step 710). The composition can include an active agent and a porous cyclodextrin-based metal organic framework (CD-MOF), the CD-MOF comprising at least a metal cation and a plurality of cyclodextrin molecules, wherein the composition comprises from about 0.05 mg to about 0.5 mg of the active agent per 1 mg of the CD-MOF, The method 700 can include applying a force to the treated area (step 720).

The amount of force applied to the treated area of skin in step 720 is selected to facilitate the mechanical release of the active agent from the CD-MOF complex. For example, in some embodiments, the amount of force applied to the composition can be force from rubbing or scrubbing the composition on the treated area using the subject's own finger or hand or an applicator stick or other object without causing pain to the treated area.

Other embodiments are within the scope of the following claims.

Those skilled in the art to which this application relates will appreciate that other and further additions, deletions, substitutions and modifications may be made to the described embodiments.

What is claimed is:

1. A composition, comprising:
   an active agent; and
   a porous cyclodextrin-based metal organic framework (CD-MOF), the CD-MOF comprising at least a metal cation and a plurality of cyclodextrin molecules;
   wherein:
   the composition comprises:
      from at least about 0.2 mg to about 0.75 mg of the active agent per 1 mg of the CD-MOF, and
      a carrier that is a mixture of an oil solvent and an aqueous solvent having a weight ratio in a range from about 10:90 to about 90:10, wherein
   a release profile of the active agent from the composition is such that a time to release at least 50 percent of a total amount of the active agent released in 24 hours is at least about 1 hour.

2. The composition of claim 1, wherein the composition comprises from at least about 0.3 mg to about 0.5 mg of the active agent per 1 mg of the CD-MOF.

3. The composition claim 1, wherein the active agent has a water solubility of at least about 10 mg/mL at 25° C.

4. The composition of claim 1, wherein the active agent is an acid, a vitamin, a pro-vitamin, a humectant, an antibacterial agent, or an antifungal agent.

5. The composition of claim 1, wherein the active agent is an alpha hydroxy acid, ascorbic acid, niacinamide, panthenol, vitamin C, vitamin B, triethylene glycol, tripropylene glycol, propylene glycol, polypropylene glycol, glycerin, sorbitol, hexylene glycol, butylene glycol, urea, a sulfonamide, tetracycline hydrochloride, triclosan, bacitracin, polymyxin B, neomycin, gentamycin, meclocycline, sulfacetamide sodium, an imidazole, a triazole, or a thiazole.

6. The composition of claim 1, wherein the active agent is a keratolytic agent, an antibacterial agent, an antifungal agent, an antiviral agent, an antiparasitic agent, a sunscreen agent, a vitamin, a pro-vitamin, an antipruritic agent, an analgesic agent, an anesthetic agent, or a nonsteroidal anti-inflammatory drug.

7. The composition of claim 1, wherein the active agent is a beta hydroxy acid, benzoyl peroxide, allantoin, sulfur, a sulfonamide, a mupirocin, erythromycin, clindamycin, acyclovir, penciclovir, docosanol, selenium disulfide, zinc pyrithione, permethrin, lindane, crotamiton, oxybenzone, avobenzone, octisalate, octocrylene, homosalate, octinoxate, retinol, retinol palmitate, tocopherol, tocotrienol, benzocaine, butamben, dibucaine, lidocaine, tetracaine, pramocaine, proxymetacaine, prilocaine, diclofenac, fentanyl, capsaicin, a salicylate, an antihistamine, a corticosteroid, ibuprofen, or naproxen.

8. The composition of claim 1, wherein the composition of the active agent and the CD-MOF is at least about 10 wt % to at most about 90 wt % of the carrier.

9. The composition of claim 1, wherein the CD-MOF has an average particle size of from about 10 nm to about 1 μm and the composition is a suspension, emulsion or a gel.

10. The composition of claim 1, wherein the CD-MOF has an average particle size of from about 1 μm to about 1 cm and the composition is an emulsion or a gel.

11. A method, comprising:
treating a subject's skin with a composition to form a treated area on the skin, wherein the composition includes:
an active agent; and
a porous cyclodextrin-based metal organic framework (CD-MOF), the CD-MOF comprising at least a metal cation and a plurality of cyclodextrin molecules, wherein the composition comprises from at least about 0.2 mg to about 0.75 mg of the active agent per 1 mg of the CD-MOF, and
a carrier that is a mixture of an oil solvent and an aqueous solvent having a weight ratio in a range from about 10:90 to about 90:10; and
applying water to the treated area, wherein a release profile of the active agent from the composition is such that the composition releases 50 wt % of the active agent of a total amount of the active agent released in 24 hours at least about 1 hour after the application of the water to the treated area.

12. The method of claim 11, wherein the composition comprises from at least about 0.3 mg to about 0.5 mg of the active agent per 1 mg of the CD-MOF.

13. The method of claim 11, wherein the composition releases at least about 50 wt % of the total amount of the active agent in the composition at 24 hours after the application of the water to the treated area.

14. A method, comprising:
treating a subject's skin with a composition to form a treated area on the skin, wherein the composition includes:
an active agent; and
a porous cyclodextrin-based metal organic framework (CD-MOF), the CD-MOF comprising at least a metal cation and a plurality of cyclodextrin molecules, wherein the composition comprises from at least about 0.2 mg to about 0.75 mg of the active agent per 1 mg of the CD-MOF, and
a carrier that is a mixture of an oil solvent and an aqueous solvent having a weight ratio in a range from about 10:90 to about 90:10; and
applying a force to the treated area, wherein a release profile of the active agent from the composition is such that the composition releases 50 wt % of a total amount of the active agent released in 24 hours at least about 1 hour after the application of the force to the treated area.

15. The method of claim 14, wherein the composition comprises from at least about 0.3 mg to about 0.5 mg of the active agent per 1 mg of the CD-MOF.

16. The method of claim 14, wherein the composition releases at least about 50 wt % of the total amount of the active agent in the composition at 24 hours after the application of the force to the treated area.

* * * * *